(12) United States Patent
Pham et al.

(10) Patent No.: US 6,451,330 B1
(45) Date of Patent: Sep. 17, 2002

(54) HIGH SKIN FRICTION COSMETIC CREAMS WITH RETINOIDS

(75) Inventors: Quynh Pham, Berkeley Heights, NJ (US); Yan Zhou, Montville, NJ (US); Prem Chandar, Closter, NJ (US)

(73) Assignee: Unilever Home & Personal Care, USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/916,154

(22) Filed: Jul. 26, 2001

Related U.S. Application Data

(60) Provisional application No. 60/235,641, filed on Sep. 26, 2000.

(51) Int. Cl.$^7$ ............ A61K 31/07; A61K 7/00; A61K 7/48; A61K 9/14; A61K 31/203
(52) U.S. Cl. ............ 424/401; 424/489; 424/502; 514/558; 514/772.3; 514/844; 514/846; 514/937; 514/951; 514/970
(58) Field of Search ............... 424/401, 489, 424/502; 514/558, 772.3, 844, 846, 937, 951, 970

(56) References Cited

U.S. PATENT DOCUMENTS 5,744,148 A  *  4/1998  Habif et al. ............... 424/401

OTHER PUBLICATIONS

Laufer et al., "Objective Measurement and Self–Assessment of Skin–Care Treatments", *Cosmetics and Toiletries Magazine,* vol. 111, Jun. 1996, pp. 92–96.

* cited by examiner

*Primary Examiner*—Frederick Krass
*Assistant Examiner*—Clinton Ostrup
(74) *Attorney, Agent, or Firm*—Ellen Plotkin

(57) ABSTRACT

A cosmetic composition is provided which includes at least about 2% solid asymmetric particles, a retinoid solubilized in a fluid oil and wherein the fluid oil to solid particles are present in a weight ratio such that the composition exhibits a normal force value of less than −100 milli-Newton containing a retinoid. The composition diminishes the appearance and feel of oily skin and is capable of delivering benefits associated with retinoids.

15 Claims, No Drawings

HIGH SKIN FRICTION COSMETIC CREAMS WITH RETINOIDS

This application claims priority of provisional appplication No. 60/235,641, filed on Sep. 26, 2000.

FIELD OF THE INVENTION

The invention relates to cosmetic skin creams containing a retinoid and providing a high skin friction.

BACKGROUND OF THE INVENTION

Consumers living in hot, humid climates, or consumers with oily skin, desire cosmetic products which have unique tactile properties during use. Specifically, such products should upon application to the skin, deliver a high skin friction and a matte finish to overcome the oily skin feel and shiny skin appearance. The greater the increase in skin friction, the less greasy the user perceives the product to be. See Laufer et al., Objective Measurement and Self-Assessment of Skin-Care Treatments, Cosmetics and Toiletries Magazine, Vol. 111, June 1996, pp. 92–96.

Retinoids are known to provide a wide spectrum of skin benefits such as skin lightening, wrinkle treatment, oil control. Unfortunately, retinoids are unstable, especially in the presence of water. High friction skin creams, however, employ water. Thus, there is a challenge to provide cosmetic creams delivering high skin friction, yet containing retinoids which remain sufficiently stable upon storage in the creams.

SUMMARY OF THE INVENTION

Accordingly, the present invention provides a cosmetic composition including:
(a) at least about 2% by weight of the composition of solid asymmetric particles;
(b) a retinoid solubilized in a fluid oil; and
wherein the fluid oil to the solid particles are present in a weight ratio such that the composition exhibits a normal force value of less than –100 milli-Newton (mN).

The present invention also provides a method of controlling or preventing an oily skin appearance and/or feel especially in the facial area, by applying to the skin the inventive composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, hands, legs and scalp.

The term "solid" as used herein means that the material is not fluid at 25° C.

The term "fluid" as used herein means that the material is fluid at 250° C.

Asymmetric Particles

The inventive compositions comprise asymmetric solid particles. Asymmetric is understood to mean that at least two of three dimensions on a majority of the particles are not size identical. These particles can be oval or plate-like. Average particle size along greatest length may range from 0.01 to 500 micron and preferably from 1 to 100 micron. The particles are employed in the composition to impart a cream-like viscosity. Furthermore, by virtue of being asymmetric, the particles deliver high skin friction. Suitable solid particles include but are not limited to fatty acid crystals, mica, talc, clays and mixtures thereof. The preferred solid particles are selected from the fatty acid crystals wherein fatty acid contains from 12–22 carbon atoms, because they are inexpensive and the most aesthetically acceptable. The most preferred fatty acid is stearic acid. The term "acid" as employed herein does not exclude the presence of a salt of fatty acid depending on the pH of the final composition. For instance, sodium, potassium or ammonium salts may be present. The salt amount is included in the amount of fatty acid. The inventive compositions contain at least 2% of the asymmetric solid particles, preferably at least 10%, more preferably from 10% to 20%, and optimally from 16% to 20% to obtain the best feel, appearance, and viscosity. The exact amount depends on the final composition and the nature of the other ingredients in the composition. The amount of the asymmetric solid particles, however, must be sufficient to impart the cream-like consistency to the composition, i.e. the viscosity of greater than about 40 Pascal-second (PaS) at a shear rate of one reciprocal second (1/s), preferably the viscosity is from about 40 PaS to about 200 PaS, most preferably from about 60 PaS to about 120 PaS, in order to provide a cream consistency that can be rubbed in easily.

The procedure for measuring viscosity is as follows:

Viscosity is measured using any viscometer or rheometer with a shear rate of 1/s, at an ambient temperature (20–25° C.). Such viscometers/rheometers are Brookfield, Haake, and Bohlin with cone and plate fixtures.

In the inventive compositions, the solid asymmetric particles are dispersed in water.

Retinoid Solubilized in a Fluid Oil

The inventive compositions contain a retinoid. Suitable retinoids include but are not limited to retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate and retinyl oleate.

The preferred ester for use in the present invention is selected from retinyl palmitate, retinyl acetate and retinyl propionate, because these are the most commercially available and therefore the least expensive. Retinyl linoleate and retinyl oleate are also preferred due to their efficacy.

The retinoid is employed in the inventive composition in an amount of at least about 0.001%, preferably from about 0.001% to about 10%, more preferably from about 0.01% to about 1%, optimally from about 0.01% to about 0.5% by weight of the composition.

The retinoid present in the inventive composition is solubilized in a fluid oil in order to improve the storage stability of the retinoid. Suitable fluid oils are selected in such a manner that the retinoid is soluble in an amount of at least 1 gram of retinoid per 100 grams of the oil at 25° C. Preferably the retinoid is soluble in an amount of at least 10 grams of the retinoid per 100 grams of the oil, most preferably 50 grams of the retinoid per 100 grams of the oil.

As an illustration, solubility of retinol crystals in varying oils is as follows:

| OIL | SOLUBILITY, WT % |
|---|---|
| Mineral oil | 34.2 |
| Cetiol OE | 45 |
| Isostearyl palmitate | 44 |
| C12–15 Alkyl benzoate | 85 |
| Triolein/Squalene (6:1) | 56.4 |
| Cyclomethicone | 2.7 |
| Dimethicone | 0.49 |

Retinoid solubility in oil is determined by the following procedure. A known weight of pure retinoid in excess of the expected solubility limit in the oil is added in an oil and methanol is added to the mixture to dissolve all retinoid crystals. Nitrogen sparging is used to ensure all methanol has evaporated from the oil. Retinoid is allowed to recrystallize overnight. The sample is filtered through a 0.45 micron filter. Known dilutions of the filtrate in isopropanol are measured by UV spectroscopy at an appropriate wavelength (325 nm for retinol) and the concentration of retinoid determined against calibration standards of retinoid in isopropanol.

Suitable fluid oils include but are not limited to esters of fatty acids or alcohols and hydrocarbons, preferably monoesters of fatty acids or alcohols, as long as they satisfy the solubility requirements described herein. Most preferably, fluid oil is selected from the group consisting of isostearyl palmitate, tridecyl salicylate, C12–15 octanoate, isopropyl stearate, isopropyl myristate and isopropyl palmitate, or any mixtures thereof. Dicapryl ether such as with a trade name, Cetiol OE, is also included as most preferable oil.

Silicone oils may be also included in the compositions. These are preferably chosen from cyclic or linear polydimethylsiloxanes containing from about 3 to about 9, preferably from about 4 to about 5, silicon atoms. Other silicone oils may be also included, such as polyalkyl siloxanes, polyalkylaryl siloxanes and polyether siloxane copolymers (e.g. dimethicone copolyol). The polyalkyl siloxanes useful herein include, for example, polydimethyl siloxanes with viscosities of from about 5 to about 100,000 centistokes at 25° C., preferably, polydimethyl siloxanes having viscosities from about 10 to about 400 centistokes at 25° C.

The oils may be employed singly or in mixtures with one another.

The oils are employed in such amounts as to dissolve the selected amount of a retinoid and yet to not compromise the high skin friction of the inventive compositions.

Skin Friction/Normal Force

The skin friction is measured by normal force. Normal force is the force exerted by the material in the axial direction during shearing flow. Normal forces arise when the material (product) microstructure becomes anisotropic under flow. Negative normal forces are generated by a decrease in bulk "volume" such as shear-induced ordering. Materials exhibiting this behavior are crystalline phases (e.g. fatty acids), rods, platelets, liquid crystals, and surfactant lamellar mesophases.

Measurement Procedure

Normal forces are measured using a controlled strain rheometer which a shearing force capability and normal force transducer (e.g. ARES (Advanced Rheometric Expansion System) from Rheometrics Corporation. Samples are compressed between parallel plates of diameters 25 or 50 mm and gap (distance between two plates) of 20 to 200 microns (most preferred 100 microns). The measurements are made in a shear step mode, and the test is divided into two zones. In the first zone (usually set for 30 to 120 seconds), the shear rate is zero and a normal force baseline is measured. In the second zone (again 30 to 120 seconds), a high shear rate is set (typically 100 to 20000 s-1, most preferred 10000 s-1), and the normal force as a function of time is monitored. The normal force is calculated as the difference between the force baseline at zero-shear and the force generated by shear. A negative difference of less than −100 milli-Newton is correlated to products/materials with the draggy sensation (high skin friction). Measurements are conducted at room temperature (20–25° C.).

The inventive compositions have the normal force of less than about −100 milli-Newton, preferably less than −200 milli-Newton, most preferably in order to obtain the most desired high skin friction, less than about −100 milli-Newton. Advantageously the normal force ranges from −200 to −1000 milli-Newton.

Typically, in order to obtain such high skin friction and to maintain solubility of the retinoid and the viscosity of the composition, the ratio of the fluid oil to the asymmetric solid particles in the composition is in the range of from about 1:1 to about 1:25, more preferably from 1:2 to 1:20, most preferably from 1:10 to 1:18. Generally, the excess of solid particles is employed when compared to the amount of the fluid oil.

Stability of the Compositions

The inventive compositions exhibit substantially improved stability of the retinoid in the composition. Specifically, the half-life of the retinoid in the compositions is preferably at least about 20 days at 50° C., more preferably at least about 40 days at 50° C., most preferably at least about 70 days at 50° C.

Determination of Retinoid Half-Life

"Half-life" is defined as the time it takes for retinoid to degrade to half of its original concentration at a given temperature.

Formulations are placed in an oven at 50° C. for an accelerated stability study. Retinoid is analyzed on time intervals for stability evaluation by a HPLC method described below. The studies showed that retinoid degradation followed a first order kinetics. Therefore, to determine the reaction half lifetime, the natural logarithm of remaining retinoid concentration is plotted against storage time to obtain a straight line with a slope k. The slope k is the rate of retinoid oxidation in reciprocal unit of time. The half lifetime of retinol is then determined by the ratio ln2/k.

The Procedure of Retinoid HPLC Analysis

A Waters Millipore system with Millennium32 software and with a photodiode array detector is used to collect the HPLC data. The chromatographic conditions are as follows:

| | |
|---|---|
| Column: | Phenonaenex I nertsil 5µ ODS 2 |
| | 150 × 4.60 mm |
| Flow rate: | 1.0 mL/min |
| Injection volume: | 30 µL |
| UV detection: | 325 nm with Photodiode Array |
| Mobile phase: | 90/10 methanol/water |
| Run time: | 15 mm |
| Temperature: | 4° C. |
| Retention time: | ca. 8.7 min. |

In order to prepare the sample solution to have a final retinoid concentration within the standard curve range, less than 10 ppm, 0.02 g cream samples is mixed with 2.5 g water first and vortexed to form a slurry. Then, methanol is added to the slurry to obtain a final total weight of 50 ml and vortexed again. The sample is subsequently filtered using a disposable syringe fitted with a 0.45 µm filter. All samples are prepared in triplicate for HPLC analysis.

Optional Skin Benefit Materials and Cosmetic Adjuncts

The inventive compositions most preferably further include an ingredient selected from the group consisting of antioxidants, reducing agents, chelating agents, and mixtures thereof to improve the stability of a retinoid. These ingredients provide an additional level of protection against oxidation of retinoilds. Common examples of antioxidants, reducing agents and chelating agent for the present formulations can be found in the CTFA International Cosmetic Ingredient Dictionary $4^{th}$ Edition, The Cosmetic, Toiletry, and Fragrance Association, Inc., Washington, D.C., 1991.

Preferable reducing agents are sodium sulfite, sodium bisulfite, sodium metabisulfite, sodium thiosulfite or other thiols, such as thioglycerol, thiourea, thioglycolic acid, cysteine and the like.

Preferable antioxidants are rac-6-hydroxy-2,5,7,8-tetramethylchromane-2-carboxylic acid (trolox), propyl gallate, n-propyl trihydroxybenzoate, t-butyl hydroquinone and butylated hydroxytoluene (BHT), butylated hydroxyanisole (BHA), tocopheryl acetate, ascorbyl palmitate, hydroquinone, dibutyl hydroquinone and the like.

Suitable examples of chelating agents include, but are not limited to, EDTA, citric acid, tartaric acid, organo aminophosphonic acids and organo phosphonic acid.

Organo aminophosphonic acid is an organic compound comprising of at least one phosphonic acid group, and at least one amino group. Suitable organo aminophosphonic acid components for use herein include the amino alkylene poly (alkylene phosphonic acids) and nitrilo trimethylene phosphonic acids. Examples of this type of organo aminophosphonic acid components include certain of the commercially available Dequest™ compounds, marketed by Monsanto.

Preferred are amino tri (methylene phosphonic acid) (Dequest 2006®), diethylene triamine penta (methylene phosphonic acid) and hexamethylene diamine tetra (methylene phosphonic acid).

Other suitable additional heavy metal ion sequestrants for use herein include nitrilotriacetic acid and polyaminocarboxylic acids such as ethylenediaminotetracetic acid, or ethylenetriamine pentacetic acid.

Still other suitable additional heavy metal ion sequestrants for use herein are iminodiacetic acid derivatives such as 2-hydroxyethyl diacetic acid or glyceryl imino diacetic acid.

Antioxidants are included in the inventive compositions in an amount of from 0.01 to 10%, preferably from 0.1 to 5%, most preferably from 0.2 to 4%. Reducing agents are included in the inventive compositions in an amount of from 0.01 to 10%, preferably from 0.1 to 5%, most preferably from 0.2 to 4%. Chelating agents are included in the inventive compositions in an amount of from 0.01 to 1%, preferably from 0.05 to 0.5%, most preferably from 0.05 to 0.3%.

The especially preferred compositions include 0.1% bisulfite, 0.7% Dequest 2006® and 0.2% BHT.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, skin lightening agents, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as Oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells. In keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo- γ-linolenic acid, columbinic acid, eicosa-(n-6, 9,13)-trienoic acid, arachidonic acid, γ-linolenic acid, timnodonic acid, hexaenoic acid and mixtures thereof.

Other optional ingredients may include coloring agents, opacifiers and pigments (e.g. titanium dioxide, silica) and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The composition can be packaged in a container suitable for its viscosity and intended use by the consumer. For example, a composition can simply be stored in a non-deformable bottle or squeeze container, such as a tube or a lidded jar.

The following specific examples further illustrate the invention, but the invention is not limited thereto.

EXAMPLES 1–3

Typical formulations according to the present invention are outlined in Table I below.

TABLE I

| | | Examples (wt. %) | | |
|---|---|---|---|---|
| Phase | Ingredients | 1 | 2 | 3 |
| A | Stearic acid | 17.9 | 17.9 | 16.5 |
| A | Cetostearyl alcohol | 0.53 | 0.53 | 0.53 |
| A | Dimethicone (DC 200, 350) | 0.5 | 0.5 | 0.5 |
| A | Parsol 1789 ® | 0.40 | 0.40 | 0.40 |
| A | Propyl Paraben | 0.10 | 0.10 | 0.10 |
| A | BHT | 0.20 | 0.20 | 0.20 |
| B | water | 73.89 | 64.54 | 71.54 |
| B | Glycerin | 1.0 | 1.0 | 1.0 |
| B | EDTA | 0.04 | 0.04 | 0.04 |
| B | Methyl Paraben | 0.20 | 0.20 | 0.20 |
| B | Potassium Hydroxide (27%) | 2.20 | 2.20 | 2.20 |
| B | Titanium Dioxide | | 0.75 | 0.75 |
| B | Silica | | 1.60 | 1.60 |
| B | Dequest ® 2006 (41%) | 0.49 | 0.49 | 0.49 |
| B | Sodium bisulfite | 0.20 | 0.20 | 0.20 |
| C | Retinol/Retinyl ester | 0.10 | 0.10 | 0.10 |
| C | Cetiol OE | 1.0 | 8.0 | — |
| C | Mineral oil | — | — | 2.4 |
| C | Parsol MCX ® | 1.25 | 1.25 | 1.25 |
| NORMAL FORCE MEASUREMENT | | | | |
| | Normal force (milli-Newtons) | −1250 | −3500 | −400 |

The formulations presented under Table I are prepared in the following fashion. Phase A is heated at 80° C. Phase B is heated to 75° C. in a container separate from that of Phase A. Thereafter the phases are combined with mixing with heat being turned off after 30 minutes. Phase C is heated to 50° C. and mixed into Phases A/B over a 10 minute period. The combination is then homogenized to 30 minutes.

Normal force measurements appearing under Table I as well as those in the subsequent Examples were measured in the following manner. Samples were compressed between parallel plates of diameter of 25 mm and gap of 100 micron. Measurements were made in a shear sweep mode with a shear rate range from 0 to 10,000 sec$^{-1}$. The normal force value was calculated as the difference between the force at zero shear rate and force at highest shear rate.

EXAMPLES 4–6

A set of comparative experiments were conducted to demonstrate the special advantages of formulating to achieve a normal force value of less than about −100 milli-Newton. The components of Examples 4 and 5 are outlined in Table II below. Although identical in formula, each was prepared in a slightly different physical manner as reported below.

TABLE II

Formula for Examples 4 and 5

| Phase | Ingredients | Wt. % |
|---|---|---|
| A | Deionized Water | 77.6 |
| A | Methyl Paraben | 0.15 |
| A | Disodium EDTA | 0.05 |
| A | Glycerine USP | 1.00 |
| A | Potassium Hydroxide (22% Active) | 2.20 |
| B | Stearic acid | 17.9 |
| B | Cetiol OE | 1.00 |
| C | Retinol | 0.10 |

PROCEDURE TO PREPARE EXAMPLE 4

1. Heat Phase A to 80° C.
2. Heat Phase B to 80° C.
3. Add Phase B to A and mix with heat off until cool to below 38° C.

PROCEDURE TO PREPARE EXAMPLE 5

1. Mix Phase A and B at room temperature for 4 hours
2. Homogenize for 10–20 min.

Typical of compositions outside the present invention having positive normal force is Example 6 whose components are listed in Table III.

TABLE III

| Phase | Ingredients | Wt. % |
|---|---|---|
| A | Deionized water | 71.68 |
| A | Magnesium Aluminum Silicate | 0.60 |
| A | Methyl Paraben | 0.15 |
| A | Disodium EDTA | 0.05 |
| A | Antifoam Emulsion | 0.01 |
| A | Butylene Glycol | 3.00 |
| A | Natrosol 250 HHR | 0.50 |
| A | Glycerine USP | 2.00 |
| A | Xanthan Gum | 0.20 |
| A | Triethanolamine (99%) | 1.20 |
| B | Stearic acid | 3.00 |
| B | Propyl Paraben | 0.10 |
| B | Naturechem GMHS ® | 1.50 |
| B | Lanette 18 DEO ® | 1.50 |
| B | Isostearyl Palmitate | 6.00 |
| B | C12–Cl5 Alkyl Octanoate | 3.00 |
| B | Silicone Fluid 200 (50 cts) | 1.00 |
| B | Cholesterol | 0.50 |
| B | Arlacel 60 | 1.00 |
| B | BHT | 0.05 |
| B | Vitamin E Acetate | 0.10 |
| B | MYRJ 59 ® | 2.00 |
| B | Pationic SSL ® | 0.50 |
| C | Hydroxycaprylic Acid | 0.10 |
| C | Retinol Palmitate | 0.06 |
| C | Alpha Bisabolol | 0.20 |

PROCEDURE TO PREPARE EXAMPLE 6

1. Heat Phase A to 80° C.
2. Heat Phase B to 75° C. in a separate container
3. Add B to A and mix with heat off for 30 min.
4. At 50° C. add Phase C and ix for 10 min.

Table IV lists the normal force values measured for Examples 4–6.

TABLE IV

| EXAMPLE | NORMAL FORCE (milli-Newtons) |
|---|---|
| 4 | −840 |
| 5 | −50 |
| 6 | +160 |

Table V lists the results of a panel test evaluation for sensory properties. Seven panelists were involved in the assessment. The following scale of assessment was employed: 0=none; 1=slight; 2=light; 3=medium and 4=high.

TABLE V

| Panelist # | Example 4 Skin friction* score | Example 4 Oily score | Example 5 Skin friction score | Example 5 Oily score | Example 6 Skin friction score | Example 6 Oily score |
|---|---|---|---|---|---|---|
| 1 | 4 | 0 | 2 | 0 | 1 | 4 |
| 2 | 4 | 0 | 2 | 0 | 0.5 | 5 |
| 3 | 5 | 0 | 2 | 0 | 0 | 4 |
| 4 | 4 | 0 | 3 | 0 | 0 | 2 |
| 5 | 4 | 0 | 2 | 1 | 1 | 4 |
| 6 | 3 | 0 | 2 | 1 | 1 | 3 |
| 7 | 4 | 1 | 1 | 0 | 1 | 3 |
| Average score | 4 | 0.14 | 2 | 0.28 | 0.64 | 3.6 |

*skin friction stands for the draggy feel of the skin

The normal force value information from Table IV and the panel sensory information from Table V reveals that for values of −50 milli-Newton and above (Examples 5 and 6), skin friction property was relatively inferior and skin feel was more oily as compared with the formulation of −840 milli-Newton (Example 4).

What is claimed is:

1. A cosmetic composition consisting essentially of:
   (a) at least about 2% by weight of the composition of solid asymmetric particles;
   (b) a retinoid solubilized in a fluid oil; and
   wherein the fluid oil to the solid particles are present in a weight ratio such that the composition exhibits a normal force value of less than −100 milli-Newton at room temperature and shear rates of about 100 s$^{-1}$ to 20,000 s$^{-1}$.

2. The composition of claim 1, wherein the solid particles are crystalline.

3. The composition of claim 1 wherein the viscosity of the composition is greater than about 40 Pascal-seconds at a shear rate of one reciprocal second (1/s) and ambient temperature.

4. The composition of claim 1 wherein the composition comprises at least about 10% by weight of the composition of the solid particles.

5. The composition of claim 1 wherein the amount of retinoid is at least about 0.001% by weight of the composition.

6. The composition of claim 1 wherein the retinoid is selected from the group consisting of retinoic acid, retinol, retinyl esters and retinal.

7. The composition of claim 1 wherein the weight ratio of the fluid oil to the solid particles ranges from about 1:1 to about 1:25.

8. The composition of claim 1 wherein the retinoid is soluble in the fluid oil in an amount of at least about 1 g of the retinoid per about 100 g of the oil at 25° C.

9. The composition of claim 1 wherein half-life of the retinoid in the composition is at least about 20 days at 50° C.

10. The composition of claim 1 wherein the retinoid is selcted from the group consisting of retinoic acid and retinal.

11. The composition of claim 1 wherein the retinoid is the $C_{16}$ ester of retinol.

12. The composition of claim 1 wherein the retinoid is selected from the group consiting of retinyl palmitate, retinyl formate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, and mixtures thereof.

13. The composition of claim 1 wherein the solid particles are selected from the group consisting of fatty acid particles, mica, talc, clays and mixtures thereof.

14. The composition of claim 13 wherein the solid particles are particles of a fatty acid containing from 12 to 22 carbon atoms.

15. the method for controlling or treating an oily skin appearance and feel by applying to the skin a cosmetic composition consisting essentially of:
   (a) at least about 2% by weight of the composition of solid asymmetric particles;
   (b) a retinoid solubilized in a fluid oil, and
   wherein the fluid oil to the solid particles are present in a weight ratio such that the composition exhibits a normal force value of less than −100 milli-Newton at room temperature and shear rates of about 100 s$^{-1}$ to 20,000 s$^{-1}$.

* * * * *